United States Patent [19]

Pardridge

[11] Patent Number: 5,004,697
[45] Date of Patent: Apr. 2, 1991

[54] CATIONIZED ANTIBODIES FOR DELIVERY THROUGH THE BLOOD-BRAIN BARRIER

[75] Inventor: William M. Pardridge, Pacific Palisades, Calif.

[73] Assignees: Univ. of CA, Calif.; Alkermes, Pa.

[21] Appl. No.: 85,627

[22] Filed: Aug. 17, 1987

[51] Int. Cl.$^5$ .............................................. A61K 39/00
[52] U.S. Cl. .................... 436/547; 424/85.8; 435/7.23; 530/389; 530/391
[58] Field of Search ............... 424/85.8; 530/391, 389; 436/548; 435/7

[56] References Cited

PUBLICATIONS

Bergmann et al., Endocrinology, 116:1729–1733, 1985.
Pardridge, The J. of Inf. Dis., vol. 158, No. 3, Sep. 1988, pp. 630–632.
Kunagai et al., J.B.C., vol. 262, No. 31, Nov. 5, 1987, pp. 15214–15219.
Triguero et al., PNAS, U.S.A., vol. 86, Jun. 1989, pp. 4761–4765.
Pardridge et al., the J. of Pharm. & Exp. Therapeutics, vol. 251, No. 3, 1989, pp. 821–826.
Klecker et al., Clin. Pharmacol Ther., Apr. 1987, pp. 407–412.
Pietra et al., Annals. N.Y. Academy of Sciences, 1982, pp. 241–247.
Spector et al., J. of Neurochemistry, 1982, pp. 837–841.
Cornford et al., BBA, 394 (1975), pp. 211–219.
Brenner et al., N.E.J.M., Apr. 13, 1978, pp. 826–833.
William M. Pardridge, "Receptor-Mediated Peptide Transport Through the Blood-Brain Barrier", Dept. of Medicine, Div. of Endocrinology, UCLA, Endocrine Reviews, 1986, vol. 7, No. 3, pp. 314–330.
Wei-Chiang Shen and Hughes J. -P. Ryser, "Conjugation of Poly-L-Lysine to Albumin and Horseradish Peroxidase: A Novel Method of Enhancing the Cellular Uptake of Proteins", Proc. Natl. Acad. Sci., U.S.A., vol. 75, No. 4, pp. 1872–1876, Apr. 1978.
Diane E. Griffin and Joseph Giffels, "Study of Protein Characteristics That Influence Entry Into the Cerebrospinal Fluid of Normal Mice and Mice with Encephalitis", J. Clin. Invest., The American Society for Clinical Investigation, Inc., vol. 70, Aug. 1982, pp. 289–295.
William M. Pardridge, M.D., "Rapid Binding and Internalization of Cationized Albumin by Isolated Brain Capillaries" (also by A. K. Kumagai and J. Eisenberg, Clin. Research, Feb. 1986).
William M. Pardridge, Arno K. Kumagai and Jody B. Eisenberg, "Chimeric Peptides as a Vehicle for Peptide Pharmaceutical Delivery Through the Blood-Brain Barrier", Biochemical and Biophysical Research Communications, vol. 146, No. 1, 1987, pp. 307–313.

*Primary Examiner*—Howard E. Schain
*Assistant Examiner*—Choon P. Koh
*Attorney, Agent, or Firm*—Poms, Smith, Lande & Rose

[57] ABSTRACT

The rate of trancytosis of antibodies across the blood-brain barrier is increased by cationizing the antibodies to provide cationized antibodies having an isoelectric point of between about 8.0 to 11.0. The increased rates of transport across the blood-brain barrier makes such cationized antibodies useful for both neurodiagnostic and neuropharmaceutical purposes. Methods for preparing such cationized antibodies are disclosed.

9 Claims, 2 Drawing Sheets

CATIONIZED ANTIBODIES FOR DELIVERY THROUGH THE BLOOD-BRAIN BARRIER

This invention was made with Government support under Grant No.: DK 25744 with the National Institutes of Health and the University of California. The Government has certain rights in this invention.

BACKGROUND OF THE INVENTION

The present invention relates generally to the use of antibodies for treatment and diagnosis of neurological diseases. More particularly, the present invention deals with the modification of antibodies so that they can be delivered through the blood-brain barrier by transcytosis.

Antibodies in general, and especially monoclonal antibodies, are widely used in diagnostic tests as a means for detecting the presence of specific antigens. Enzyme linked immunoassay and radioimmunoassay are common diagnostic techniques which utilize antibodies and detect antigens in vivo. Antigens may also be detected in vitro by administering radiolabelled antibodies to a living subject followed by external detection of radiolabelled antibody sequestered by a particular organ bearing the respective antigen. Antibodies have also been used widely in the treatment of viral infections and other diseases. However, the use of antibodies in either the treatment or diagnosis of neurological diseases has been very limited because most antibodies are not capable of traversing the blood-brain barrier (BBB) and entering the brain.

The vertebrate brain has a unique capillary system which is unlike that in any other organ in the body. The unique capillary system has morphologic characteristics which make up the blood-brain barrier. The blood-brain barrier acts as a system wide cellular membrane which separates the brain interstitial space from the blood. The unique morphologic characteristics of the brain capillaries which make up the blood-brain barrier are: (a) epithelial-like high resistance tight junctions which literally cement all endothelia of brain capillaries together, and (b) scanty pinocytosis or transendothelial channels, which are abundant in endothelia of peripheral organs. Due to the unique characteristics of the blood-brain barrier, antibodies that readily gain access to other tissues in the body are barred from entry into the brain or their rates of entry are very low.

Few strategies have been developed for introducing these antibodies into the brain which otherwise would not cross the blood-brain barrier. The most commonly used strategy involves an invasive procedure where the antibody is delivered directly into the brain. The most common procedure is the implantation of a catheter into the ventricular system to bypass the blood-brain barrier and deliver the antibody directly to the brain. Such a procedure has been used in treating echovirus encephalitis (Erlendsson et al., Successful Reversal of Echovirus Encephalitis in X-linked Hypogammablobulinemia by Intraventricular Administration of Immunoglobulin. 1985. New England Journal of Medicine. Vol. 312, No. 6. pages 351-353).

Although invasive procedures, such as the one described above, for the direct delivery of antibodies to the brain ventricles have experienced some success, they are not entirely satisfactory because they do not deliver the antibodies to the structures deep within the brain. Further, the invasive procedures are potentially harmful to the patient. Accordingly, there presently is a need to provide an improved method for delivering antibodies across the blood-brain barrier and into the brain for both diagnostic and therapeutic purposes.

SUMMARY OF THE INVENTION

In accordance with the present invention, a method is provided for introducing antibodies directly across the blood-brain barrier by transcytosis. The invention is based upon the discovery that cationized antibodies cross the blood-brain barrier at much higher rates than normal non-cationized antibodies.

The effectiveness of antibodies for both neurodiagnostic and neuropharmaceutical purposes is increased by cationizing the antibodies to provide cationized antibodies having an isoelectric point (pI) of between about 8.0 to 11.0. These highly basic antibodies cross the blood-brain barrier at rates which are much higher than the trancytosis rates for normal acid and neutral antibodies which typically have isoelectric points in the range of 5 to 6. This provides an effective means for delivering antibodies into the brain by trancytosis rather than by the previously used direct invasive methods.

The cationized antibodies in accordance with the present invention are prepared by treating a given monoclonal or polyclonal antibody with a cationization agent such as hexamethylenediamine. The cationization agent replaces surface carboxyl groups on the antibody with a more basic group, such as a primary amine group in the case of hexamethylenediamine and related amine compounds. The amount of cationization agent and reaction conditions are controlled so that the resulting cationized antibody has an isoelectric point of between about 8.0 to 11.0 and preferably between about 8.0 to 9.0.

As one feature of the present invention, the immunoreactivity of the antibodies is preserved during cationization by first reacting the antibody with an excess of a corresponding antigen to block the immunoreactive sites on the antibody. These blocked immunoreactive sites are unreactive during the subsequent cationization steps. The antigens are then decoupled from the cationized antibodies after the cationization step to thereby reactivate the blocked immunoreactive sites.

The cationization of antibodies in accordance with the present invention is useful whenever it is necessary to introduce an antibody into the brain. Both neurodiagnostic and neurotherapeutic uses for antibodies is contemplated. Particular diagnostic uses include diagnosis of Alzheimer's disease, brain tumors or any other diagnostic use where a labeled or tagged antibody is introduced into the brain for reaction with and detection of specific antigens. Therapeutic uses include treatment of viral infections of the brain or other diseased conditions where introduction of an antibody into the brain is required to treat the disease.

The above discussed and many other features and attendant advantages of the present invention will become apparent as the invention becomes better understood by reference to the following detailed description.

DETAILED DESCRIPTION OF THE INVENTION

Figure 1:
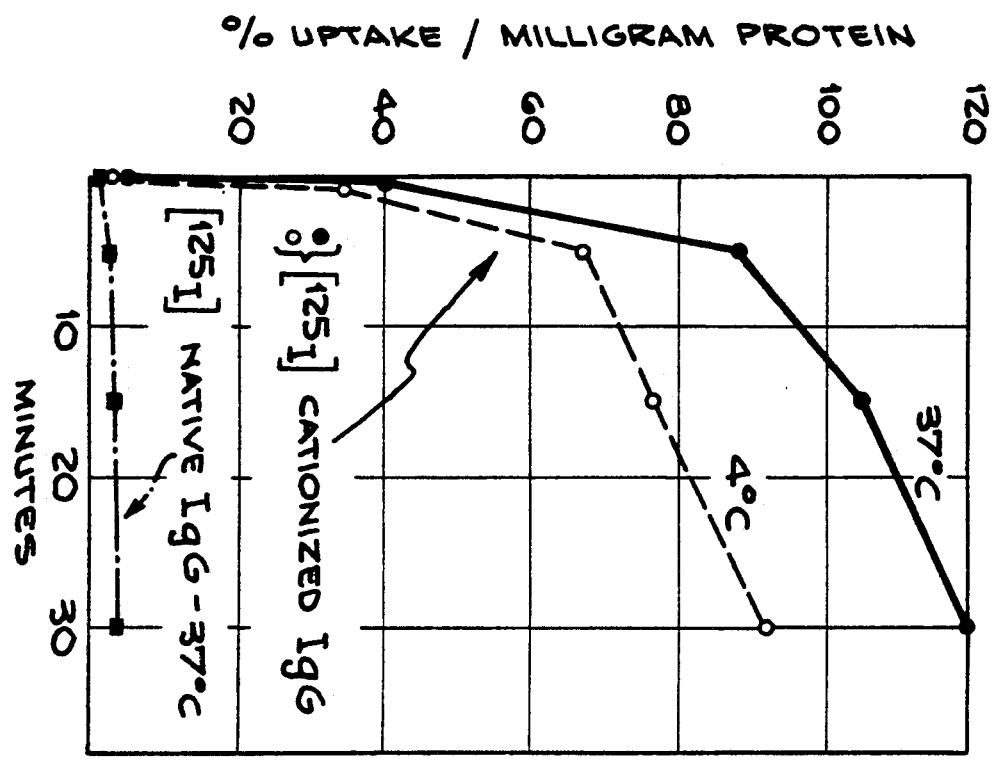
FIG. 1 is a graph showing the increase in uptake of cationized IgG by brain capillaries at both 4° C. and 37° C. The results are expressed as percent uptake of IgG per milligram of IgG.

The present invention involves the transport of antibodies through the brain capillary wall, i.e. the blood-brain barrier (BBB). The nature of the blood-brain barrier and problems associated with transport of peptides and proteins therethrough is set forth in "Receptor-Mediated Peptide Transport through the Blood-Brain Barrier" (W. M. Pardridge, Endocrine Reviews, Vol. 7, No. 3, August 1986, pages 314–330), the contents of which is hereby incorporated by reference.

The present invention has wide application to any antibody which is useful in diagnosing or treating brain disorders. Antibodies in general do not readily cross the blood-brain barrier. This is due to the acidic or neutral character of antibodies. It was discovered that the uptake or transport of antibodies into the brain can be greatly increased by cationizing the antibodies to form cationized antibodies having an isoelectric point of between about 8.0 to 11.0.

Antibodies are proteins which have both positive and negative charges with the number of each depending upon the pH of the antibody solution. The pH at which the positive and negative charges are equal is called the "isoelectric point" (pI). Techniques for measuring the pI of a given antibody or protein are well known and generally involve isoelectric focusing according to conventional electrophoresis procedure. As previously mentioned, most antibodies have an isoelectric point of between about 5 to 6.

The relatively low isoelectric point of antibodies is due to the presence of carboxyl groups on the surface of the antibodies. The present invention involves substituting basic groups in place of a sufficient number of surface carboxyl groups to increase the pI of the antibody to between about 8.0 to 11.0. Isoelectric points of between about 8.0 to 9.0 are preferred with isoelectric points of around 8.5 being especially preferred. The degree of cationization should be as high as possible without causing the antibody to form into aggregates. Higher pI's are preferred because the rate of transport of the antibody across the blood-brain barrier increases with increasing pI. However, this must be offset by the increasing possibility of antibody aggregate formation at higher levels of cationization.

Cationization of the antibody can be carried out according to any of the known procedures for displacing surface carboxyl groups on proteins with basic cations. Preferred cationization agents include amine compounds such as hexamethlyenediamine and related amine compounds. Hexamethylenediamine is the preferred cationization agent because it is widely available and the techniques for its use in cationizing proteins are well known. The amount of cationizing agent and the conditions for reaction with the antibody can be varied so long as the final cationized antibody has a pI within the above-mentioned range required for blood-brain barrier transport.

The particular antibodies which can be used are virtually unlimited, provided that they have some diagnostic or therapeutic use in connection with the brain. Monoclonal antibodies are preferred because of their increased diagnostic or therapeutic potential. Typical antibodies which can be cationized for blood-brain barrier transcytosis are antibodies to one or more of the antigenic portions of peptides specific to Alzheimer's disease (Pardridge, W. M. et al., Amyloid Angiopathy of Alzheimer's Disease: Amino Acid Composition and Partial Sequence of a 4,200 - Dalton Peptide Isolated from Cortical Microvessels, Journal of Neurochemistry, 1987, pages 001–008). Antibodies to such specific peptides can be tagged with a radioactive tracer or other identifier and then cationized to a pI of 8.5 with hexamethylenediamine. The resulting tagged and cationized antibody can then be administered intravenously to the patient using a suitable pharmaceutically acceptable carrier solution. The tagged and cationized antibody will cross the blood-brain barrier and enter the brain where it will bind to any of the peptides which are unique to Alzheimer's disease. Detection of the bond tagged and cationized antibody which is bound to the specific peptides is then performed by convention of neuroimaging techniques, such as external detection nuclide counting.

Other diagnostic antibodies which can be cationized to provide entry into the brain include antibodies for use in detecting various types of brain tumors. For example, monoclonal antibodies to tumor specific proteins such as glial fibrillary acidic protein (GFAP) can be prepared by conventional and well known techniques for monoclonal antibody preparation. Antibodies to human DR antigen and human immunodeficiency virus HIV antigen are other examples.

The resulting monoclonal antibodies are treated with hexamethylenediamine or other cationization agents to increase the pI of the antibody to between about 8.0 to 11.0. The antibody can be tagged with a radioactive tracer prior to or after the cationization process. The resulting tumor specific cationized and tagged antibody is then administered to the patient intravenously for transport across the blood-brain barrier and binding to any tumor specific antigen. Detection of bound antibody is again accomplished by convention radionuclide scanning techniques.

Cationized antibodies for use in treating viral diseases such as AIDS or other disorders of the brain can also be prepared as set forth above. Once an antibody (preferably monoclonal) is prepared for a specific neurotropic virus or other infectious agent, the antibody is cationized to increase its pI to between about 8.0 to 11.0. The antibody is then administered intramuscularly or intravenously to the patient. The antibody is typically administered as a solution of antibody in a suitable pharmaceutical carrier such as saline buffer. The doses of cationized antibody administered for either diagnostic or therapeutic purposes will parallel the dosage levels established for non-cationized antibodies. Typical dosages range from 0.01 mg to 1 mg for diagnostic purposes and from 1 mg to 100 mg for therapeutic purposes.

Preferred antibodies include chimeric human antibody molecules designed to have reduced antigeneity, such as those antibodies having mouse antigen-binding domains with human constant region domains. Such chimeric antibodies have been disclosed by S. L. Morrison et al. (Chimeric Human Antibody Molecules: Mouse Antigen-binding Domains with Human Constant Region Domains, Proc. Nat'l. Acad. Sci. U.S.A., November 1984, Vol. 81, pages 6851–6855).

Although hexamethylenediamine is the preferred compound for use in cationizing antibodies, other cationizing agents are possible. For example, ethylene diamine, N,N-dimethyl-1,3-propanediamine, or polylysine may be used. Cationization is catalyzed by carboxyl activation using N-ethyl,N[1](3-dimethyl-aminopropyl) carbodiimide hydrochloride (EDAC) using the method described by Hoare and Koshland (A Method for the Quantitative Modification and Estimation of Carboxylic Acid Groups in Proteins. 1967. *J. Biol. Chem.* 342:2447-2453).

In order to prevent reductions in the immunoreactivity of an antibody during cationization, it is preferred that the antibody be pre-bound to the antigen of interest prior to cationization. This pre-binding with antigen effectively blocks the immunoreactive sites on the antibody and prevents them from being cationized. After cationization is complete and the pI of the antibody has been raised to the desired level between about 8.0 to 11.0, the cationized antibody is then treated to unbind the antigen from the antibody. The unbinding is accomplished according to well known procedures where the antibody-antigen complex is treated with an acid to break the antibody-antigen bond. The antibody is then recovered by column chromatography or other conventional separation and recovery technique.

As an example of practice, bovine IgG was cationized and tested against native bovine IgG as follows:

One gram of bovine immunoglobulin G was dissolved in 10 ml of water followed by dialysis at 4° C. overnight against water. To this was added slowly 67 ml of 2M hexamethylenediamine while stirring, and the pH was kept at 7.8. Thirty minutes later, 1 g of EDAC was added and the pH was maintained at 7.8 and the solution was stirred at room temperature for 3-4 hours. The material was then dialyzed against 40 liters of water overnight at 4° C. followed by evaporation to dryness the following day.

The cationized antibody and native bovine antibody were then radiolabelled with $^3$H-sodium borohydride using standard methods which have been described previously by Pardridge et al. (Absence of Albumin Receptor on Brain Cappillaries In Vivo or In Vitro. 1985, *Am. J. Physiol.* 249:E264-E267; Chimeric Peptides as a Vehicle for Peptide Pharmaceutical Delivery through the Blood-Brain Barrier. 1987, *Biochem. Biophys. Res. Commun.* 146:307-315). Bovine brain capillaries were isolated from fresh bovine brain and used as in vitro model system of the blood-brain barrier as reviewed by Pardridge, W. M. (Receptor-Mediated Peptide Transport through the Blood-Brain Barrier. 1986, *Endocrine Reviews* 7:314-330).

Figure 2:
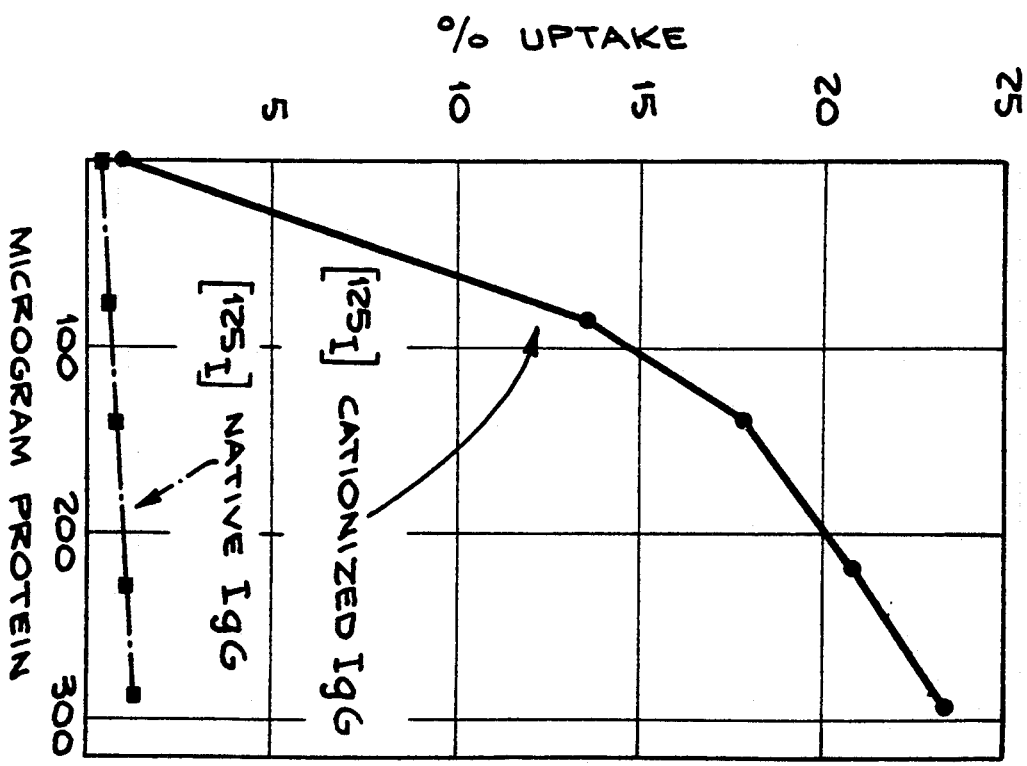
FIG. 2 is a graph which also shows the increase in uptake of cationized IgG by brain capillaries. The results are expressed as percent uptake of IgG versus amount of brain capillaries.
Figure 3:
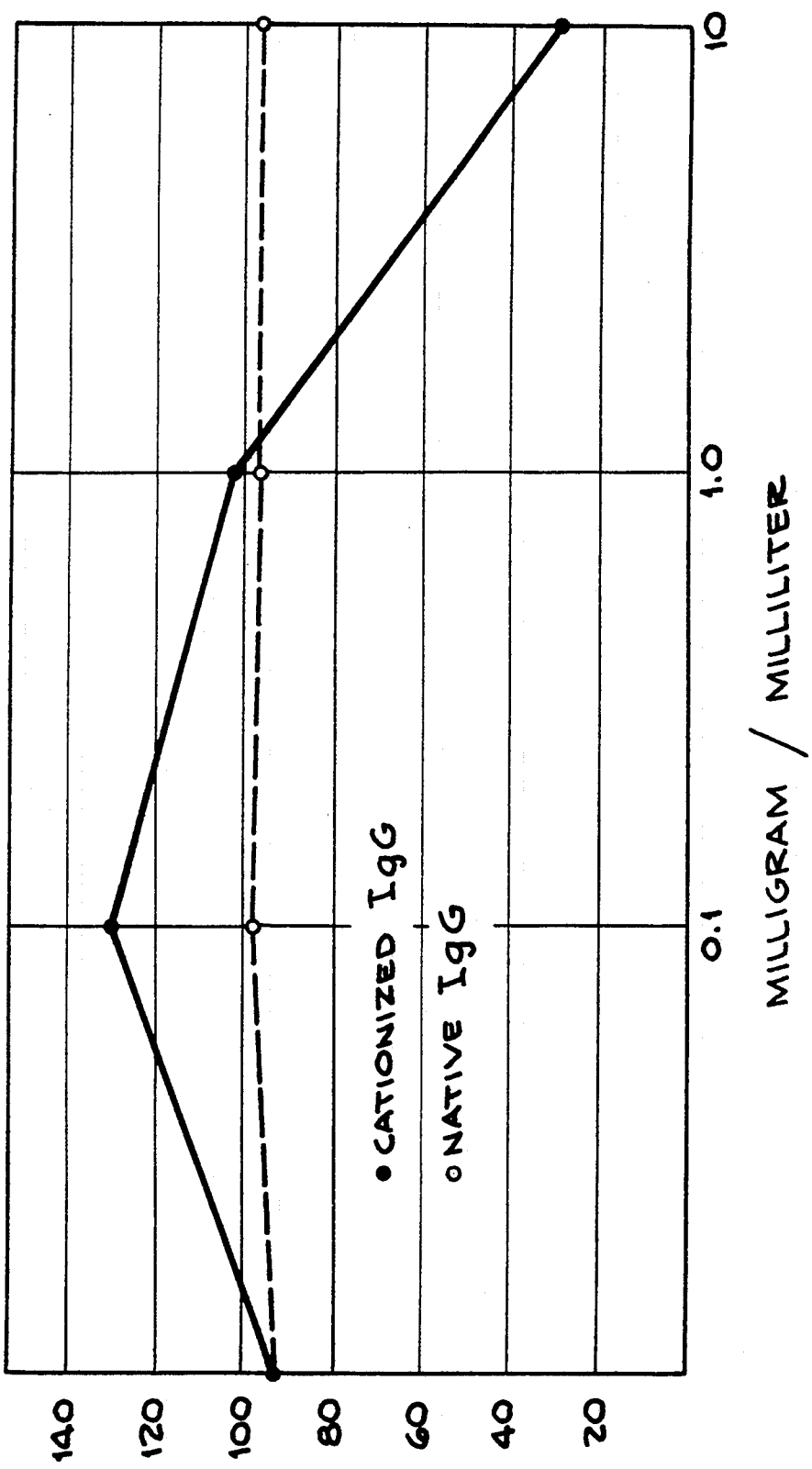
FIG. 3 is a graph showing the uptake of cationized IgG plotted versus the concentration of either native IgG or cationized IgG.

The results of the above tests with bovine IgG are set forth in FIGS. 1, 2 and 3. In FIG. 1, the percent uptake per milligram protein of ($^{125}$I) cationized IgG or ($^{125}$I) native IgG at either 37° C. or 4° C. is plotted versus incubation time. The labeled cationized or native IgG was incubated with isolated bovine brain capillaries, which are used as an in vitro model system of blood-brain barrier transport. The results show that the cationization procedure increases the uptake of the IgG by nearly 50-fold, and that this is partially inhibited by cold temperatures. In FIG. 2, the percent uptake of ($^{125}$I) cationized IgG or ($^{125}$I) native IgG is plotted versus the amount of bovine brain capillary protein content in micrograms per tube. There is approximately a 25-fold increase in the uptake of the IgG following cationization.

In FIG. 3, the percent uptake of ($^{125}$I) cationized IgG per milligram protein of isolated bovine brain capillary is plotted versus the concentration of unlabeled cationized IgG or native IgG. The data show that the uptake of ($^{125}$I) cationized IgG is completely independent of concentration of native IgG through three log orders of magnitude in concentration. However, the presence of unlabeled cationized IgG stimulates the uptake in low concentrations and greatly depresses the uptake in high concentrations. The concentration of cationized IgG which causes 50% inhibition is approximately 2.5 mg/ml or approximately 15 uM cationized IgG.

Further examples of practice are:

A monoclonal antibody may be prepared against a synthetic peptide corresponding to the 4200 Dalton amyloid peptide of Alzheimer's disease amyloid angiopathy (see Pardridge et al, Amyloid angiopathy of Alzheimer's disease: amino acid composition and partial sequence of a 4,200-Dalton peptide isolated from cortical microvessels, 1987 *J. Neurochem* 49.) This amyloid is deposited on the brain side of the BBB and, thus, a monoclonal antibody to the amyloid peptide cannot be used as a neuroimaging device unless the monoclonal antibody is transportable through the BBB. The monoclonal antibody to the synthetic amyloid peptide may be cationized using hexamethylenediamine and EDAC, in the presence of saturated concentrations of synthetic amyloid peptide (to protect the active antigen binding sites on the antibody), to an isoelectric point of between 8-11. The cationized antibody may then be separated from the antigen by gel filtration in the presence of 0.1M glycine (pH=2.5). The high molecular weight peak containing the cationized antibody is then neutralized to pH=7.4 and is now suitable for radiolabelling using standard radionuclides such as technetium 99m or iodine-I$^{131}$.

A monoclonal antibody to human GFAP may be prepared by isolating GFAP from human autopsy brain using standard techniques or by isolating recombinant human GFAP from either a bacterial or a eukaryotic expressing system. The monoclonal antibody to GFAP may then be cationized using hexamethylenediamine and EDAC in the presence of high concentrations of GFAP, followed by separation of cationized antibody from antigen as described above. The cationized monoclonal antibody to human GFAP may then be radiolabelled with technetium 99m or iodine-I$^{131}$ or other conventional radionuclides. The final preparation is a radiolabelled antibody to GFAP that is transportable through the BBB and may be used as a neuroimaging device for early detection of brain glial tumors.

Another example is the preparation of mouse-human chimeric antibody directed against the human DR-antigen. This mouse-human chimeric antibody may be cationized using hexamethylenediamine and EDAC in the presence of saturating concentrations of recombinant DR-antigen followed by separation of cationized antibody from the free DR-antigen. The cationized human-mouse chimeric monoclonal antibody to the human DR-antigen may then be administered subcutaneously to subjects with demyelinating diseases, such as multiple sclerosis, that have an immune basis, and the pathogenesis of which may be ameliorated by the administration of antibody against the DR-antigen. For example, Sriram and Steinman (Anti I-A Antibody Suppresses Active Encephalomyelitis: Treatment Model for Diseases Linked to IR Genes. 1983, *J. Exp. Med.* 158:1362-1367) have provided evidence that immune linked demyelinating diseases may be treated by administration of antibody against the class II histocompatibility antigen.

Having thus described exemplary embodiments of the present invention, it should be noted by those skilled in the art that the within disclosures are exemplary only and that various other alternatives, adaptations and modifications may be made within the scope of the present invention. Accordingly the present invention is not limited to the specific embodiments as illustrated herein, but is only limited by the following claims.

What is claimed is:

1. In a diagnostic composition comprising one or more antibodies for administration to an individual for neurodiagnostic purposes, said antibodies having a relatively low transfer rate across the blood-brain barrier, wherein the improvement comprises cationizing said antibodies to provide cationized antibodies having an isoelectric point of between about 8.0 and 11.0, said cationized antibodies having increased rates of transfer across said blood-brain barrier.

2. A diagnostic composition according to claim 1, wherein said antibodies are monoclonal antibodies.

3. A diagnostic composition according to claim 2 wherein the isoelectric point of said cationized antibodies is between about 8.0 to 9.0.

4. A diagnostic composition according to claim 1 wherein said antibody is an antibody to an Alzheimer's disease amyloid peptide.

5. A diagnostic composition according to claim 1 wherein said antibody is an antibody to one or more antigens present in GFAP protein.

6. In a neuropharmaceutical composition comprising one or more antibodies for administration to an individual for neurotherapeutic purposes, said antibodies having a relatively low transfer rate across the blood-brain barrier, wherein the improvement comprises cationizing said antibodies to provide cationized antibodies having an isoelectric point of between about 8.0 and 11.0, said cationized antibodies having increased rates of transfer across said blood-brain barrier.

7. A neuropharmaceutical composition according to claim 6 wherein said antibodies are monoclonal antibodies.

8. A neuropharmaceutical composition according to claim 7 wherein the isoelectric point of said cationized antibodies is between about 8.0 to 9.0.

9. A neuropharmaceutical composition according to claim 6 wherein said antibody is an antibody to an antigen selected from the group consisting of amyloid peptide of Alzheimer's disease, human GFAP, human DR-antigen, or the human immunodeficiency virus (HIV).

* * * * *

UNITED STATES PATENT AND TRADEMARK OFFICE
CERTIFICATE OF CORRECTION

PATENT NO. : 5,004,697
DATED : April 2, 1991
INVENTOR(S) : William M. Pardridge and Paul R. Schimmel It is certified that error appears in the above-identified patent and that said Letters Patent is hereby corrected as shown below:

On the title page, item [75]:

Please add the second inventor's name --Paul R. Schimmel, Lexington, Mass.--

Signed and Sealed this

Eleventh Day of August, 1992

Attest:

DOUGLAS B. COMER

*Attesting Officer*      *Acting Commissioner of Patents and Trademarks*